United States Patent [19]
Viola et al.

[11] Patent Number: 5,326,915
[45] Date of Patent: Jul. 5, 1994

[54] CATALYST GRANULES, IN PARTICULAR FOR THE OXIDATIVE DEHYDROGENATION OF METHANOL IN ORDER TO YIELD FORMALDEHYDE

[75] Inventors: Augusto Viola; Massimo Brusa; Bernardo Merighi; Giuseppe Gubitosa, all of Novara, Italy

[73] Assignee: Montecatini Tecnologie S.p.A., Milan, Italy

[21] Appl. No.: 71,655

[22] Filed: Jun. 1, 1993

Related U.S. Application Data

[62] Division of Ser. No. 984,315, Dec. 1, 1992.

[30] Foreign Application Priority Data

Oct. 6, 1992 [IT] Italy .................. MI 92A 002301

[51] Int. Cl.$^5$ .............................................. C07C 45/38
[52] U.S. Cl. ..................................... 568/474; 568/472
[58] Field of Search .................................. 568/472, 474

[56] References Cited

FOREIGN PATENT DOCUMENTS

| | | | |
|---|---|---|---|
| 1144252 | 2/1963 | Fed. Rep. of Germany | 568/474 |
| 1222032 | 8/1966 | Fed. Rep. of Germany | 568/474 |
| 7116496 | 5/1971 | Japan | 568/474 |
| 7401447 | 8/1974 | Netherlands | 568/474 |
| 1463174 | 2/1977 | United Kingdom | 568/474 |

*Primary Examiner*—Werren B. Lone
*Attorney, Agent, or Firm*—David M. Klein; Bryan Cave

[57] ABSTRACT

A configuration of cylindrical catalyst granules displays a trilobed or triangular cross-section provided with three through-bores equidistant from each other, each of which through-bores has its axis parallel to the axis of the cylindrical granule (FIG. 1).

26 Claims, 1 Drawing Sheet

CATALYST GRANULES, IN PARTICULAR FOR THE OXIDATIVE DEHYDROGENATION OF METHANOL IN ORDER TO YIELD FORMALDEHYDE

This is a divisional of U.S. application Ser. No. 07/984,315, filed Dec. 1, 1992.

The present invention relates to a novel shape for catalyst granules. In particular, it relates to a cylindrical catalyst granule of the type displaying a cross-section with at least three points of contact with a circumscribed circumference.

A catalyst in granular form for use in a fixed-bed reactor, is generally required to comply with the following requirements:
- low resistance to gas flow (low pressure drop, with the height of catalytic bed being the same);
- large actual surface-area, i.e., high ratio of surface area to volume;
- high heat exchange coefficient between catalyst particles and reaction gas;
- good mechanical strength, in order to prevent catalyst particles from undergoing breakage.

The catalysts which are normally used in fixed-bed catalytic processes display a spherical, solid-cylindrical or ring-like configuration, of various sizes. By using such shapes known from the prior art, the diffusion of the reactant gases inside the interior of catalyst particles and the back-diffusion of the reaction products into the interior of the particles result often to be very limited. This means that, inasmuch as in heterogeneous systems the reaction occurs more easily and in selective way of external catalyst surface, the catalysts having the shape known from the prior art are not used enough in a reaction.

As a consequence, in order to achieve the desired conversion rates, large amounts of catalyst have to be used and, for that purpose, in the case of tube-bundle fixed beds, tubes have to be used, which have an adequate height. With the catalysts having the shapes known from the prior art, this requirement results in a further increase in pressure drops, because the empty spaces intervening between catalyst bodies are small. Furthermore, in exothermic reactions, which generate large heat amounts—such as oxidative dehydrogenation, oxidation, halogenation and hydrogenation reactions—a high value of coefficient of heat exchange between the catalyst and the gas feed is required, in order to secure an adequate removal of reaction heat, and consequently avoid an excessive overheating of the catalytic bed, which often damages the catalyst and/or reduces the catalytic performance thereof. In the case of the catalysts having the traditional shape, in order to accomplish a high heat exchange coefficient, the turbulence of the reaction gas on catalyst particles had to be increased, but such a contrivance would cause a further increase in pressure drops, with a consequent increase in operations costs.

Catalysts by having shapes which differ from traditional shapes are disclosed in U.S. Pat. No. 4,441,990; which relates to tubular extruded granules having an essentially triangular or quadrangular, multilobed cross section. With such catalysts, some advantages are achieved in terms of breakage strength and pressure drop, but the results are really not very different from as obtainable with the traditional catalysts.

The purpose of the present invention is supply a configuration for a catalyst granule, which makes it possible which makes it possible to obtain considerably improved results in terms of pressure drop, high ratio of surface area to volume and high heat exchange coefficient.

According to the present invention, such a purpose is achieved because the granule or particle displays at least three through-bores having axes substantially parallel to each other and to the axis of the particle, and substantially equidistant from each other.

Said through-bores preferably have a circular cross section and, on the cross section of the particle, their axes define vertices of a substantially equilateral triangle, said vertices being orientated towards the points of contact of the cross section of the catalyst particle with the circumscribed circumference.

Due to the above characteristics, and owing to the particular geometry of the granules, a high turbulence of the reaction gases on the same granules can be promoted under the same operating conditions as customarily adopted in industrial facilities. As said granules display a large free surface area of their cross section, they oppose a lower resistance to the gas flow, with consequent lower pressure drops. Furthermore, their having a short equivalent diameter [equivalent diameter=6*(volume/total surface area)], results in said catalyst particles displaying a larger actual surface-area, i.e., a higher value of surface-area/volume ratio and, consequently, in a better contact of the reaction gases with the catalyst surface, which favours the conversion of the reactants, and limits the inner diffusion phenomena, with a consequent increase in selectivity. In fact, with the catalysts according to the present invention very high yields of useful product are obtained with half catalyst amounts per volume unit, as compared to catalysts with shapes known from the prior art. The bulk density of these catalysts is indeed very low (0.5-0.8 g/cm$^3$).

According to a first form of practical embodiment of the present invention, the catalyst particle displays substantially circular-cylindical lobes equal to each other, and co-axial with the through-bores.

According to a second form of practical embodiment of the present invention, the catalytic particle displays a cross-section of substantial triangular shape with rounded vertices.

In both of the above said forms of practical embodiment, the ratio of the bore pitch (wherein, by "bore pitch", the distance between the respective axes is meant), to the diameter of the same bores, is preferably comprised within the range of from 1.15 to 1.5, and, more preferably, of from 1.3 to 1.4.

The ratio of the height of the granule to the bore pitch is preferably comprised within the range of from 1.5 to 2.5, more preferably of from 1.7 to 2.3.

According to the first form of practical embodiment of the present invention, the ratio of the bending radius of each lobe to the bore pitch is preferably comprised within the range of from 0.6 to 0.9, and, more preferably, of from 0.7 to 0.8. The ratio of the bending radius of the lobes to the radius of the through-bores is preferably comprised within the range of from 1.4 to 2.4, and, more preferably, of from 1.75 to 2.05. The ratio of the radius of the circumscribed circumference to the bending radius of the circular lobes is preferably comprised within the range of from 1.6 to 2, and, more preferably, of from 1.7 to 1.85. The ratio of the surface area to the volume of each granule in the multilobed form of practical embodiment results to be preferably higher than 2.4, and, still more preferably, higher than 2.7.

According to the second form of practical embodiment of the present invention, the ratio of the bending radius of each rounded vertex to the bore pitch is preferably comprised within the range of from 0.6 to 0.9, and, more preferably, of from 0.7 to 0.8. The ratio of the radius of the circumscribed circumference to the bending radius of each rounded vertex is preferably comprised within the range of from 1.6 to 2, and, more preferably, of from 1.7 to 1.85. The ratio of the surface area to the volume of each granule in the multilobed form of practical embodiment results to be preferably higher than 3.1, and, still more preferably, larger than 3.3.

The shape of the catalyst according to the present invention lends itself to be used in a wide range of catalytic processes, such as, e.g., hydrogenation and dehydrogenation of organic compounds, alkylation or dealkylation of benzene derivatives, isomerization, conversion of olefins into methanol, thermooxidation of methane to yield olefins, and so forth.

A particularly advantageous application of the catalyst according to the invention is—when said catalyst is constituted by iron and molybdenum oxides—the use thereof in formaldehyde production process by means of the oxidative methanol dehydrogenation. According to such a process, one or more reactor(s) is(are) used in parallel, which are constituted by multi-tube bundles which contain the catalyst and operate within the temperature range of from 230° to 450° C. In such reactors, the heat developed during the reaction is exchanged through the walls, with a thermostatting fluid caused to circulate outside the tubes. The reaction tubes have small enough inner diameters (15-25 mm) and the circulation of the diathermic fluid is so accomplished, as to cause the catalytic bed to operate under conditions which are as close as possible to isothermal conditions.

In the feed gases, methanol and oxygen are present at concentrations which are lower than 9 and 12% by volume, respectively, and in such a ratio to each other that in all reactor points, the oxygen content is always higher than as stoichiometric concentration as required by the reaction ($MeOH + \frac{1}{2}O_2 \rightarrow HCHO + H_2O$; in practice, when all methanol has reacted, oxygen concentration should exceed the value of 4% by volume) and, simultaneously, is always lower than that oxygen concentration which would cause the mixture to explode (Bureau of Mines Bull., 279, 1939, pages 82-foll.).

At reactor inlet, the molar fraction of methanol to be oxidized is limited to that value above which the exothermic character of the reaction would not allow a sufficient heat exchange to take place, in order to prevent dangerous local overheating of the catalyst bed to occur ("hot spots").

In such a type of process, as constituted as reported hereinabove, the shape and the size of the catalyst are of basic importance, so that the advantages deriving from the configuration according to the present invention are particularly considerable.

Further advantages and characteristics of the catalyst according to the present invention will be evident from the following disclosure in detail, supplied for merely illustrative, non-limitative, purposes, and made by referring to the accompanying drawings, in which:

Figure 1:
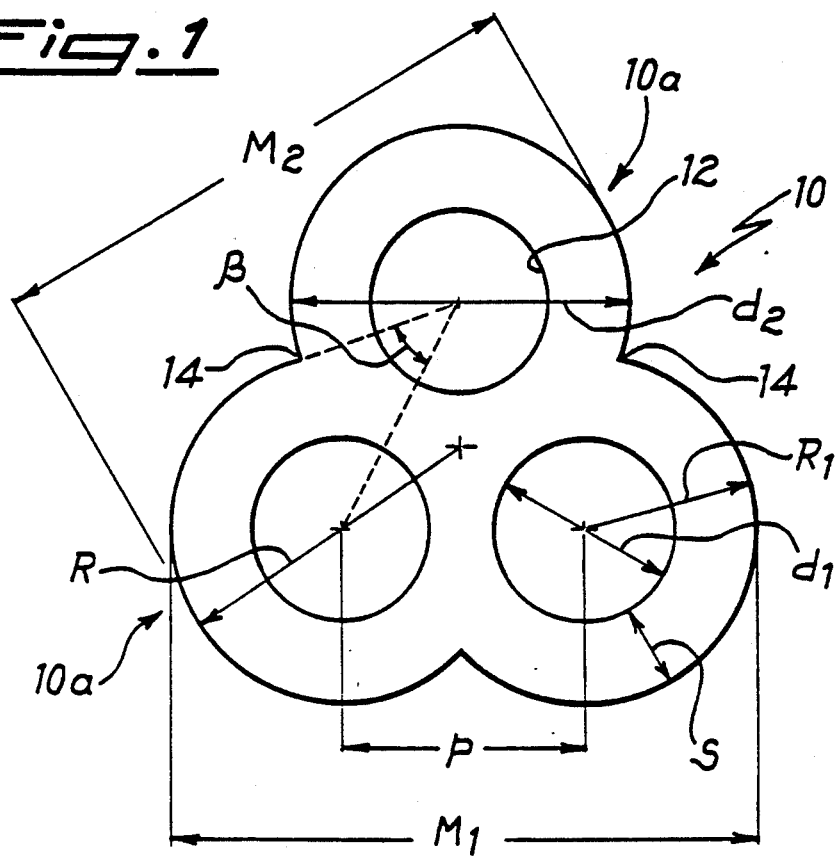
FIG. 1 is a plan view of a first form of practical embodiment of a catalytic granule according to the present invention.

Referring to the drawings, with 10 a cylindrical catalyst granule (pellet) is displayed, which is provided with three circular through-bores 12 arranged with their respective centres at the vertices of an equilateral triangle.

In the form of practical embodiment illustrated in FIG. 1, the pellet shows a trilobed cross section, with circular lobes 10a joining each other at longitudinal grooves 14 arranged along the side surface of the pellet. The bores 12, the diameter of which is indicated with $d_1$, are coaxial with the circular lobes 10a and define, together with them, walls of thickness s. With "$\beta$", the angle is indicated which is formed between the line which joins the centres of two through-bores 12, and the line which joins the centre of one of said bores with the longitudinal groove defined by the lobes 10a coaxial with both said bores. With p, the pitch between the bores 12 (i.e., the distance between their centres) is indicated, and with $d_2$ the diameter of the lobes 10a is indicated (the radius of said lobes is indicated with $R_1$). The radius of the circumscribed circumference to the cross section of the pellet is indicated with the reference R. With $M_1$ and $M_2$, the maximal and minimal dimensions of the cross section of the pellet are indicated.

Figure 2:
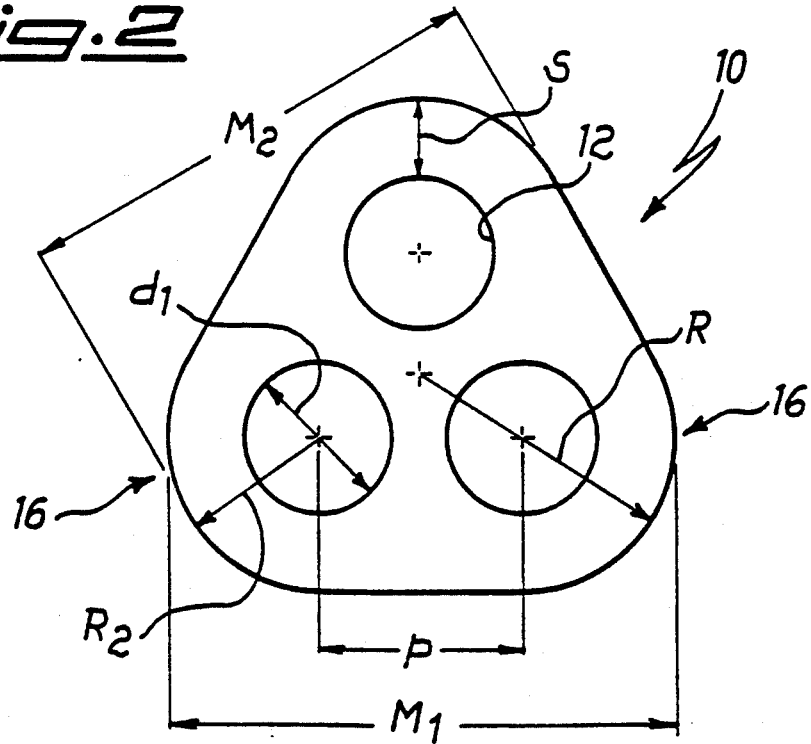
FIG. 2 is a plan view of a catalytic granule according to a second form of practical embodiment of the invention.

Referring to the form of practical embodiment illustrated in FIG. 2, and in which, as regards the dimensions, the same reference numerals and characters are used, which are used in FIG. 1, the catalyst pellet shows a triangular cross section with rounded vertices 16. The latter have a bending radius, which is indicated with $R_2$.

In Tables 1 and 2 enclosed with the instant disclosure, the size parameters are reported of catalyst pellets according to FIGS. 1 and 2, respectively; and in Table 3, the size parameters are reported of two traditional pellet types of ring-like shape, accomplished by using the fabrication technology as disclosed in the following examples. For some of such catalysts, for oxidative dehydrogenation of methanol the physical-chemical characterizations have been performed (Table 4).

From the data relevant to the dimensions and shape of this type of pellets, the volume of the solid body corresponding to the shape of one single pellet ("solid space") and from this, by determining the bulk density of the catalyst, the expected weight for each pellet is calculated. The resulting expected weight complies with the experimentally found weigh throughout the tested range of equivalent diameter values (2.32–1.76 mm).

Of course, the bulk density depends on the fabrication pressure, the characteristics of the powder used as the starting material, and the modalities of calcination.

The activity, selectivity and pressure drop values were determined in a through-flow reactor according to the procedure as described in the following examples. The operating conditions, and the results of catalyst performances are reported in Table 5. In the same Table, the results are reported which were obtained, under the same experimental conditions, with two different catalysts (Examples 13 and 14) having a traditional (ring-like) shape.

By comparing the results, one may clearly infer that with the catalyst according to the present invention, higher yields and lower pressure drops are obtained, with the catalyst volume being the same. If one considers that these novel catalysts display a lower bulk density (expressed as g/cm³), the advantage results to be even larger.

In particular, the catalysts display a high activity (Example 1; Table 5) even at relatively low temperatures; and high selectivity values (Example 9; Table 5) at relatively high temperatures.

EXAMPLES 1–14

A powder of $Fe_2(MoO_4)_3$ and $MoO_3$ was carefully mixed with stearic acid as inner lubricant, and the mixture was submitted to a forming-by-compaction process, by using a special mould in order to obtain pellets having the shape and dimensions as reported in Tables 1 and 2, or moulds of traditional shape, in order to prepare the catalysts of Comparative Examples 13 and 14 (Table 3).

The pellets were subsequently submitted to a calcination process at a temperature comprised within the range of from 500° C., to 550° C., for 4 hours.

The forming conditions were so regulated, as to obtain catalysts, after the calcination step, having the characteristics as reported in Table 4.

For the determination of the values of activity, yield and pressure drops achievable with these catalysts, a steel reactor was used which has an inner diameter of 20.4 mm and a height of 1900 mm, arranged in vertical position inside a molten-salt thermostatting bath kept agitated by means of a nitrogen stream.

The catalyst was packed inside the tubular reactor as a fixed bed of 700 mm of height.

Through the reactor a gas stream was flown (in down-flow mode) at a linear speed of 1.5 Nm/sec and with a total inlet pressure of 950 mmHg (1.25 bars), containing a methanol concentration of 6% by volume, and an oxygen concentration of 9.5% by volume. Downstream from the reactor, the outlet gas pressure was determined in order to calculate the pressure drops ($\Delta p$).

The temperature of the molten salt bath was so adjusted as to reach a methanol conversion of >98%.

The reactor exiting reaction gases were analysed by gaschromatography, by using two "Fractovap" (ex Carlo Erba) gaschromatographs. The one of them used a Poropak-T column for $CO_2$, $CH_2O$, DME (dimethyl ether), $H_2O$, unconverted MeOH determination, and on the other, $O_2$, $N_2$ and CO were determined on a column of Type-A molecular sieves.

The results are reported in Table 5.

TABLE 1

| Catalyst code | A | B | C | D | E | F | G |
|---|---|---|---|---|---|---|---|
| Height h (mm) | 5.00 | 5.00 | 5.00 | 4.00 | 4.00 | 4.00 | 4.50 |
| Angle $\beta$ (rad) | 0.89 | 0.78 | 0.75 | 0.89 | 0.78 | 0.75 | 0.78 |
| Bore diameter $d_1$ (mm) | 1.70 | 1.70 | 1.70 | 1.70 | 1.70 | 1.70 | 1.70 |
| Minimal thickness s (mm) | 0.90 | 0.80 | 0.65 | 0.90 | 0.80 | 0.65 | 0.80 |
| Bore pitch p (mm) | 2.20 | 2.35 | 2.20 | 2.20 | 2.35 | 2.20 | 2.35 |
| Maximal dimension of cross section $M_1$ (mm) | 5.70 | 5.65 | 5.20 | 5.70 | 5.65 | 5.20 | 5.65 |
| Minimal dimension of cross section $M_2$ (mm) | 5.41 | 5.34 | 4.91 | 5.41 | 5.34 | 4.91 | 5.34 |
| Solid cross section surface area (mm²) | 15.64 | 14.69 | 11.28 | 15.64 | 14.69 | 11.28 | 14.69 |
| Side surface area (mm²) | 170.77 | 171.18 | 164.28 | 136.62 | 136.94 | 131.42 | 154.06 |
| Total surface area (mm²) | 202.06 | 200.56 | 186.83 | 167.91 | 166.32 | 153.98 | 183.44 |
| Volume of space occupied by catalyst particle ("solid space") (mm³) | 78.22 | 73.46 | 56.38 | 62.58 | 58.76 | 45.11 | 66.11 |
| Equivalent diameter (mm) | 2.32 | 2.20 | 1.81 | 2.24 | 2.12 | 1.76 | 2.16 |
| Ratio of surface area/volume S/V (mm⁻¹) | 2.58 | 2.73 | 3.31 | 2.68 | 2.83 | 3.41 | 2.78 |
| Ratio of bore pitch/diameter $p/d_1$ | 1.29 | 1.38 | 1.29 | 1.29 | 1.38 | 1.29 | 1.38 |
| Lobe diameter $d_2$ (mm) | 3.5 | 3.3 | 3.0 | 3.5 | 3.3 | 3.0 | 3.3 |
| $d_2/d_1$ | 2.06 | 1.94 | 1.76 | 2.06 | 1.94 | 1.76 | 1.94 |
| Lobe radius $R_1$ (mm) | 1.75 | 1.65 | 1.50 | 1.75 | 1.65 | 1.50 | 1.65 |
| $R_1/p$ | 0.79 | 0.70 | 0.68 | 0.79 | 0.70 | 0.68 | 0.70 |
| Ratio of height/bore pitch h/p | 2.27 | 2.13 | 2.27 | 1.82 | 1.70 | 1.82 | 1.91 |
| Radius of circumscribed circumference R (mm) | 3.02 | 3.01 | 2.77 | 3.02 | 3.01 | 2.77* | 3.01 |
| $R/R_1$ | 1.72 | 1.82 | 1.85 | 1.72 | 1.82 | 1.85 | 1.82 |

TABLE 2

| Catalyst code | H | L | M | N | P | Q |
|---|---|---|---|---|---|---|
| Height h (mm) | 5.00 | 5.00 | 5.00 | 4.00 | 4.00 | 4.00 |
| Bore diameter $d_1$ (mm) | 1.70 | 1.70 | 1.70 | 1.70 | 1.70 | 1.70 |
| Minimal thickness s (mm) | 0.90 | 0.80 | 0.65 | 0.90 | 0.80 | 0.65 |
| Bore pitch p (mm) | 2.20 | 2.35 | 2.20 | 2.20 | 2.35 | 2.20 |
| Maximal dimension of cross section $M_1$ (mm) | 5.70 | 5.65 | 5.20 | 5.70 | 5.65 | 5.20 |
| Minimal dimension of cross section $M_2$ (mm) | 5.41 | 5.34 | 4.91 | 5.41 | 5.34 | 4.91 |
| Solid cross section surface area (mm²) | 16.46 | 15.77 | 12.25 | 16.46 | 15.77 | 12.25 |
| Side surface area (mm²) | 168.09 | 167.20 | 160.23 | 134.47 | 133.76 | 128.19 |
| Total surface area (mm²) | 201.00 | 198.73 | 184.74 | 167.39 | 165.29 | 152.70 |
| Volume of space occupied by catalyst particle ("solid space") (mm³) | 82.29 | 78.84 | 61.27 | 65.83 | 63.07 | 49.02 |
| Equivalent diameter (mm) | 2.46 | 2.38 | 1.99 | 2.36 | 2.29 | 1.93 |
| Ratio of surface area/volume S/V (mm⁻¹) | 2.44 | 2.52 | 3.01 | 2.54 | 2.62 | 3.11 |
| Ratio of bore pitch/diameter $p/d_1$ | 1.29 | 1.38 | 1.29 | 1.29 | 1.38 | 1.29 |
| Bending radius of vertices $R_2$ (mm) | 1.75 | 1.65 | 1.50 | 1.75 | 1.65 | 1.50 |

TABLE 2-continued

| Catalyst code | H | L | M | N | P | Q |
|---|---|---|---|---|---|---|
| $R_2/p$ | 0.79 | 0.70 | 0.68 | 0.79 | 0.70 | 0.68 |
| Ratio of height/bore pitch h/p | 2.27 | 2.13 | 2.27 | 1.82 | 1.70 | 1.82 |
| Radius of circumscribed circumference R (mm) | 3.02 | 3.01 | 2.77 | 3.02 | 3.01 | 2.77 |
| $R/R_2$ | 1.72 | 1.82 | 1.85 | 1.72 | 1.82 | 1.85 |

TABLE 3

| Catalyst Code | X | Y |
|---|---|---|
| Height (mm) | 3.80 | 5.00 |
| Outer diameter (mm) | 4.00 | 5.00 |
| Inner diameter (mm) | 2.00 | 2.50 |
| Thickness (mm) | 1.00 | 1.25 |
| Surface area of solid cross section (mm$^2$) | 9.42 | 14.73 |
| Side surface area (mm$^2$) | 71.63 | 117.81 |
| Total surface area (mm$^2$) | 90.48 | 147.26 |
| Volume of space occupied by catalyst granule ("solid space") (mm$^3$) | 35.81 | 73.63 |
| Equivalent diameter (mm) | 2.38 | 3.00 |
| Free surface area of cross section (mm$^2$) | 3.14 | 4.91 |

TABLE 4
Catalyst for Formaldehyde Physical-Chemical Characterization

| Example No. | Catalyst code | Pellet height mm | Chemical Analysis No, % by weight | Chemical Analysis Fe, % by weight | Calc. temp. °C. | Weight of 30 pellets, g | BET specific surface area, m$^2$/g | True density, g/cc | Bulk density, g/cc | Porosity, % | Total Porosity, cc/g | Average radius, Angstrom |
|---|---|---|---|---|---|---|---|---|---|---|---|---|
| 1 | B | 5.00 | 54.5 | 12.5 | 500 | 3.75 | 5.90 | 3.89 | 1.62 | 58.4 | 0.36 | 1220 |
| 2 | B | 5.00 | 54.5 | 12.5 | 500 | 4.00 | 5.90 | 3.90 | 1.75 | 55.1 | 0.32 | 1085 |
| 3 | B | 5.00 | 54.5 | 12.5 | 500 | 4.20 | 5.80 | 3.89 | 1.81 | 53.5 | 0.30 | 1034 |
| 4 | B | 5.00 | 54.5 | 12.5 | 530 | 4.15 | 4.37 | 3.93 | 1.84 | 53.2 | 0.29 | 1327 |
| 5 | B | 5.00 | 54.5 | 12.5 | 500 | 4.48 | 5.40 | 3.89 | 1.92 | 50.6 | 0.26 | 963 |
| 6 | G | 4.50 | 54.5 | 12.5 | 500 | 3.77 | 5.45 | 3.95 | 1.79 | 54.7 | 0.31 | 1128 |
| 7 | E | 4.00 | 54.5 | 12.5 | 500 | 3.35 | 5.47 | 3.93 | 1.80 | 54.2 | 0.30 | 1097 |
| 8 | B | 5.00 | 54.5 | 12.5 | 500 | 3.55 | 4.42 | 3.90 | 1.60 | 59.0 | 0.37 | 1674 |
| 9 | B | 5.00 | 54.5 | 12.5 | 530 | 3.55 | 3.73 | 3.86 | 1.61 | 58.3 | 0.36 | 1930 |
| 10 | G | 4.50 | 54.5 | 12.5 | 500 | 3.42 | 4.16 | 3.87 | 1.75 | 54.8 | 0.31 | 1490 |
| 11 | A | 5.00 | 54.5 | 12.5 | 500 | 4.00 | 5.70 | 3.85 | 1.75 | 54.55 | 0.31 | 1087 |
| 12 | A | 5.00 | 54.5 | 12.5 | 550 | 4.00 | 3.70 | 3.85 | 1.75 | 55.1 | 0.32 | 1730 |
| 13* | X | 5.00 | 54.5 | 12.5 | 500 | 1.90 | 5.30 | 3.92 | 1.78 | 55.2 | 0.31 | 1170 |
| 14* | Y | 5.00 | 54.5 | 12.5 | 500 | 3.90 | 5.62 | 3.85 | 1.83 | 53.1 | 0.29 | 1032 |

TABLE 5
Experimental Tests

Inner diameter of reactor = 20.4 mm
Height of catalyst bed = 700 mm
Linears peed = 1.5 Nm/second
MeOH concentration = 6.0% by volume
Oxygen concentration = 9.5% by volume

| Example No. | Bulk Density, g/mm | Temperature of salt bath, °C. | ΔP through the reactor, mm$_{Hg}$ | Conversion % | CH$_2$O molar yield | CO molar yield | DME molar yield | CO$_2$ molar yield |
|---|---|---|---|---|---|---|---|---|
| 1 | 0.61 | 265 | 55 | 98.75 | 94.82 | 2.79 | 1.07 | 0.07 |
| 2 | 0.65 | 270 | 45 | 98.82 | 94.68 | 3.08 | 0.94 | 0.12 |
| 3 | 0.69 | 275 | 45 | 98.75 | 94.10 | 3.40 | 0.96 | 0.09 |
| 4 | 0.69 | 290 | 45 | 99.28 | 95.22 | 3.11 | 0.82 | 0.13 |
| 5 | 0.73 | 280 | 45 | 99.12 | 93.94 | 4.19 | 0.90 | 0.09 |
| 6 | 0.69 | 270 | 50 | 98.83 | 94.42 | 3.25 | 1.07 | 0.1 |
| 7 | 0.70 | 270 | 55 | 99.06 | 94.65 | 3.31 | 0.94 | 0.08 |
| 8 | 0.69 | 280 | 40 | 98.92 | 95.61 | 2.23 | 0.98 | 0.10 |
| 9 | 0.69 | 300 | 50 | 98.76 | 96.23 | 1.66 | 0.76 | 0.12 |
| 10 | 0.65 | 280 | 40 | 98.61 | 95.54 | 2.02 | 0.92 | 0.12 |
| 11 | 0.69 | 270 | 45 | 98.76 | 94.11 | 3.60 | 0.98 | 0.07 |
| 12 | 0.69 | 310 | 50 | 98.98 | 96.10 | 2.07 | 0.71 | 0.10 |
| 13* | 0.81 | 270 | 100 | 98.98 | 94.59 | 3.25 | 0.98 | 0.15 |
| 14* | 0.73 | 280 | 50 | 98.83 | 92.31 | 5.59 | 0.83 | 0.10 |

*Comparative Example

We claim:

1. A process for the manufacture of formaldehyde comprising dehydrogenating methanol in the presence of catalyst granules at a temperature ranging from about 230° C. to about 450° C. and wherein the methanol and the oxygen present in the feed gas are kept outside of explosive limits, each catalyst granule having a cylindrical shape displaying a cross-section with at least three points of contact with a circumscribed circumference of said granules, each catalyst granule having at least three through-bores having axes which are substantially parallel to each other and to the axis of the granule, and substantially equidistant from each other, said catalyst granules comprising iron and molybdenum oxides.

2. A process according to claim 1 wherein said catalyst granule through-bores have a circular cross-section and have axes which, on the cross-section of the granule, define vertices of a substantially equilateral triangle, with said vertices being oriented towards the point of contact of the cross-section with said circumscribed circumference.

3. A process according to claim 2 wherein each catalyst granule has substantially cylindrical-circular lobes equal to each other and coaxial with said through-bores.

4. A process according to claim 2 wherein each catalyst granule has a substantially triangular cross-section with rounded vertices.

5. A process according to claim 2 wherein the ratio of the bore pitch (p) to the diameter of the same bores (d1) of each catalyst granule is within the range of 1.15 to 1.5.

6. A process according claim 2 wherein for each granule the ratio of the height of the granule to the pitch of the bores of the granule is within the range of 1.5 to 2.5.

7. A process according to claim 3 wherein for each granule the ratio of the bending radius of each lobe to the pitch of the bores is within the range of 0.6 to 0.9.

8. A process according to claim 3 wherein for each granule the ratio of the bending radius of the lobes to the radius of the through-bores is within the range of 1.4 to 2.4.

9. A process according to claim 3 wherein for each granule the ratio of the radius of the circumscribed circumference to the bending radius of each rounded vertex is within the range of 1.6 to 2.0.

10. A process according to claim 3 wherein the ratio of the surface area to the volume of each granule is greater than 2.4.

11. A process according to claim 4 wherein for each granule the ratio of the bending radius of each rounded vertex to the bore pitch is within the range of 0.6 to 0.9.

12. A process according to claim 4 wherein for each granule the ratio of the radius of the circumscribed circumference to the bending radius of each rounded vertex is within the range of 1.6 to 2.

13. A process according to claim 4 wherein the ratio of the surface area to the volume of each granule is in the range of 2.44–3.11.

14. A process according to claim 1 wherein said catalyst granules derive from powders based on $Fe_2(MoO_4)_3$ and $Mo_3$.

15. A process according to claim 1 wherein said catalyst granules are contained in a fixed-bed reactor, said granules reacting with said mixture of methanol and oxygen in said fixed-bed reactor.

16. A process according to claim 15 further comprising the step of providing more than one of said fixed-bed reactors, each of said more than one fixed-bed reactors being configured in parallel with each other, each of said fixed-bed reactors being provided with a supply of said catalyst granules, and said mixture of methanol and oxygen being directed over said granules in each of said reactors.

17. A process according to claim 15 wherein said fixed-bed reactor comprises multi-tube bundles, and said catalyst granules being contained in said multi-tube bundles.

18. A process according to claim 16 wherein each of said fixed-bed reactors comprises multi-tube bundles, and said catalyst granules being contained in said multi-tube bundles in each reactor.

19. A process according to claim 16 wherein said dehydrogenation occurs within the temperature range of 230° to 450° C.

20. A process according to claim 17 wherein said multi-tube bundles comprise a plurality of reaction tubes each of said reaction tubes having an inner diameter of 15-25 mm.

21. A process according to claim 18 wherein said multi-tube bundles comprise a plurality of reaction tubes each of said reaction tubes having an inner diameter of 15-25 mm.

22. A process according to claim 20 further comprising the step of circulating a diathermic fluid around said reaction tubes.

23. A process according to claim 21 further comprising the step of circulating a diathermic fluid around said reaction tubes.

24. A process according to claim 15 wherein said mixture of methanol and oxygen comprises methanol at lower than 9% by volume, and oxygen at lower than 12% by volume.

25. A process according to claim 24 wherein the oxygen content in said fixed-bed reactor is always higher than the stoichiometric concentration as required by the reaction $MeOH + \frac{1}{2}O_2 \rightarrow HCHO + H_2O$.

26. A process according to claim 15 wherein the oxygen content in said fixed-bed reactor is always higher than the stoichiometric concentration as required by the reaction $MeOH + \frac{1}{2}O_2 \rightarrow HCHO + H_2O$.

* * * * *